(12) United States Patent
Elsbury

(10) Patent No.: US 9,149,311 B2
(45) Date of Patent: Oct. 6, 2015

(54) CERVICAL PLATE FIXATION SYSTEM

(71) Applicant: Andrew Elsbury, Fortville, IN (US)

(72) Inventor: Andrew Elsbury, Fortville, IN (US)

(73) Assignee: Nexxt Spine, LLC, Noblesville, IN (US)

( * ) Notice: Subject to any disclaimer, the term of this patent is extended or adjusted under 35 U.S.C. 154(b) by 0 days.

(21) Appl. No.: 14/485,756

(22) Filed: Sep. 14, 2014

(65) Prior Publication Data

US 2015/0005821 A1 Jan. 1, 2015

Related U.S. Application Data

(63) Continuation of application No. 12/504,408, filed on Jul. 16, 2009, now Pat. No. 8,834,536.

(51) Int. Cl.
A61B 17/80 (2006.01)
A61B 17/70 (2006.01)

(52) U.S. Cl.
CPC ......... *A61B 17/8057* (2013.01); *A61B 17/7059* (2013.01); *A61B 17/8052* (2013.01)

(58) Field of Classification Search
CPC .................. A61B 17/8057; A61B 17/8052
See application file for complete search history.

(56) References Cited

U.S. PATENT DOCUMENTS

| 2004/0260306 A1* | 12/2004 | Fallin et al. ................. 606/104 |
| 2007/0043366 A1* | 2/2007 | Pfefferle et al. ............... 606/69 |
| 2008/0140130 A1* | 6/2008 | Chan et al. .................. 606/280 |

* cited by examiner

Primary Examiner — David Bates

(57) ABSTRACT

A bone fixation assembly comprises a plate having a top surface and a bottom surface and defining at least one bone screw bore, the bore including a circumferential rib situated between the top and bottom surfaces of the plate and at least one scallop interrupting the circumferential rib. A bone engaging fastener is provided for each bore, the fastener having a shank defining bone engaging threads and an enlarged head. The head defines threads for threaded engagement with the circumferential rib, with a lead thread configured to pass through a scallop to allow the threads to engage the circumferential rib.

20 Claims, 4 Drawing Sheets

CERVICAL PLATE FIXATION SYSTEM

PRIORITY CLAIM AND REFERENCE TO RELATED APPLICATION

The present application is a continuation of and claims priority to application Ser. No. 12/504,408, filed on Jul. 16, 2009, which issued on Sep. 16, 2014, as U.S. Pat. No. 8,834,536.

BACKGROUND

The present invention relates to fixation systems for use in stabilizing and immobilizing spinal segments, particularly in the cervical spine.

Bone fixation devices are useful for promoting the proper healing of injured or damaged spinal motion segments caused by trauma, tumor growth, degenerative disc disease or other spinal pathologies that may necessitate permanent immobilization. These fixation devices are typically used to immobilize the injured/damaged bone or motion segments to ensure the proper growth of new osseous tissue between the damaged segments.

One type of fixation system utilizes an osteosynthesis plate, more commonly referred to as a bone plate that can be used to immobilize adjacent skeletal parts such as vertebral bones. Typically, the fixation plate is a rigid metal or polymeric plate positioned to span bones or bone segments that require immobilization with respect to one another. The plate is fastened to the respective bones using anchors, such as bone screws, so that the plate remains in contact with the bones and fixes them in a desired position. Cervical plates, for instance, can be useful in providing the mechanical support necessary to keep vertebral bodies of the cervical spine in proper position, and in bridging a weakened or diseased area such as when a disc, vertebral body or spinal fragment has been removed. These cervical plates usually include a rigid bone plate having a plurality of screw openings in the form of holes or slots that allow for freedom of screw movement. The bone plate is placed against the damaged vertebral bodies and bone screws are used to secure the bone plate to the spine, usually with the bone screws being driven into the vertebral bodies. Cervical bone plates are typically placed anteriorly, although posterior or transverse fixation is also known.

Because the cervical spine is routinely subject to mechanical loads which cycle during movement, one of the primary concerns is the risk of screw pullout. This is of particular concern in the cervical region because of the critical vessels that abut the anterior surfaces of the cervical spine. Screw pullout often occurs when the cylindrical portion of the bone which surrounds the inserted screw fails. A bone screw which is implanted perpendicular to the plate is particularly weak because the region of the bone which must fail for pullout to occur is only as large as the outer diameter of the screw threads. It has been found that for pullout to occur for a pair of screws which are angled relative to each other and to the plate, the amount of bone which must fail increases substantially as compared to pairs of screws which are implanted in parallel along the axis that the loading force is applied. It has, therefore, been one goal of those in the art to provide a cervical screw-plate assembly that permits the screws to be entered into the vertebral body at angles other than 90 degrees.

As mentioned above, a great concern with screws being implanted in the anterior portion of the cervical spine is that there are important internal tissue structures which may be damaged by a dislocated screw. In the cervical spine, the esophagus is located directly in front of the anterior surface of the vertebral body, and therefore, in potential contact with an implanted cervical plate. Because screw pullout represents one of the largest risks of esophageal perforation, it has been a further goal object of those in the art to produce a cervical screw-plate design that prevents the screw from separating from the plate, even if the bone holding the screw fails.

One typical screw-plate design provides angled holes for insertion of the bone screw. This typical design, as represented by the Orion® Anterior Cervical Plate System of Sofamor Danek, further includes an additional threaded hole disposed between pairs of bone screw holes so that a corresponding set screw may be inserted to lock the bone screws to the plate. Although the Orion® system achieved certain advantages over prior cervical screw plate assemblies, one drawback is that a given plate can accommodate only one screw angular orientation per hole. This is undesirable, in that physicians often must inspect the vertebral bodies during the implantation procedure before making the decision as to which screw-in angle is the ideal. While providing a variety of plates having different angle bone screw holes is possible, the complexity and expense of providing a full spectrum of plates available in the operating room for the surgeon to choose from is undesirable.

In order to address the concerns of these screw-plate systems, other systems have been developed that permit polyaxial coupling of the screw to the plate, whereby a single plate is compatible with a wide range of screw-in angles. In typical systems of this type, the head of the bone screw is spherical to match a spherical surface on the holes formed in the cervical plate. The bone screw can thus be oriented at a wide range of angles relative to the plate. In other systems, the bone screw is seated within an insert that is mounted within the screw holes in the plate, wherein the insert permits the variable angle placement of the screw. In both systems, a separate component, such as a set screw, is required to lock the assembly in position and prevent back-out of the bone screw from the plate.

There remains a need for an orthopedic screw plate assembly which provides an effective mechanism for engaging a bone screw to the plate at any desired angular orientation. It is desirable that the assembly require as few parts as possible to simplify the surgeon's task during implantation into the cervical spine.

SUMMARY

In one embodiment, a bone fixation assembly comprises a plate having a top surface and a bottom surface and defining at least one bore between the surfaces adapted to receive a bone engaging fastener therethrough. Each bore includes an inner surface and a circumferential rib projecting therefrom the inner surface and situated between the top and bottom surfaces of the plate. Each bore further defines at least one scallop interrupting the circumferential rib.

The fixation assembly further comprises a bone engaging fastener corresponding to each of the bores, the fastener having a shank defining bone engaging threads and an enlarged head. The head defines locking threads for threaded engagement with the circumferential rib. The locking threads include a lead thread that is configured to pass through a scallop to allow the remaining threads to engage the circumferential rib.

In one specific embodiment, each bore defines at least three scallops substantially evenly distributed around the circumference of the circumferential rib. The scallops allow the bone engaging fastener to achieve different angles relative to the plate and at different azimuthal positions based on which scallop the lead screw engages first.

In a further embodiment, the plate is a substantially rectangular plate sized and shaped for fixation between at least two adjacent cervical vertebrae. The plate includes four bone screw bores, one each situated at each corner of the substantially rectangular plate. Four bone engaging fasteners are provided for engagement within a corresponding one of the four bores. In this embodiment, each of the four bores is substantially identically configured and each of the four bone engaging fasteners is substantially identically configured so that each bone fastener can adopt variable angular orientations relative to the plate as dictated by the cervical anatomy.

In one feature, the circumferential rib defines an inner edge and the bore further defines a scallop run-out extending tangentially from a scallop to the inner edge. The scallop run-out merges substantially tangentially with the inner edge. In one aspect, the run-out forms a sharp corner with the next adjacent scallop. The sharp corner prevents the head of the fastener from backing out of the bore. In a specific embodiment, each bore defines at least three scallops substantially spaced apart 120 degrees around the circumference of the circumferential rib with each scallop including a corresponding scallop run-out extending from the scallop and merging with the inner edge about 80 degrees from the scallop.

According to a further aspect, a method is provided for engaging a fixation plate to a bone that comprises the step of providing a fixation plate having a top surface and a bottom surface and defining at least one bore between the surfaces, the bore including an inner surface and a circumferential rib projecting from the inner surface and situated between the top and bottom surfaces of the plate, and the bore further defining at least one scallop interrupting the circumferential rib. In a further step, a bone engaging fastener is provided corresponding to each of the at least one bore, the fastener having a shank defining bone engaging threads and a head, the head defining threads for threaded engagement with the circumferential rib, the threads including a lead thread configured to pass through the scallop to allow the threads to engage the circumferential rib.

The method further comprises positioning the fixation plate on the bone with the bottom surface contacting the bone, passing the shank of the bone engaging fastener through the bore, driving the shank of the bone engaging fastener into the bone at any angle relative to the fixation plate until the lead thread of the head of the fastener is within the bore, and rotating the fastener so that the lead thread passes through a scallop in the bore. The fastener is rotated until the head of the fastener is fully seated within the bore.

The present invention provides an improved bone fixation assembly, and more particularly an assembly that allows engagement of a bone fastener at multiple angular orientations. The fixation assembly further provides means for locking the fastener to the bone plate so that the assembly does not loosen over time.

DESCRIPTION OF THE EMBODIMENTS

Figure 1:
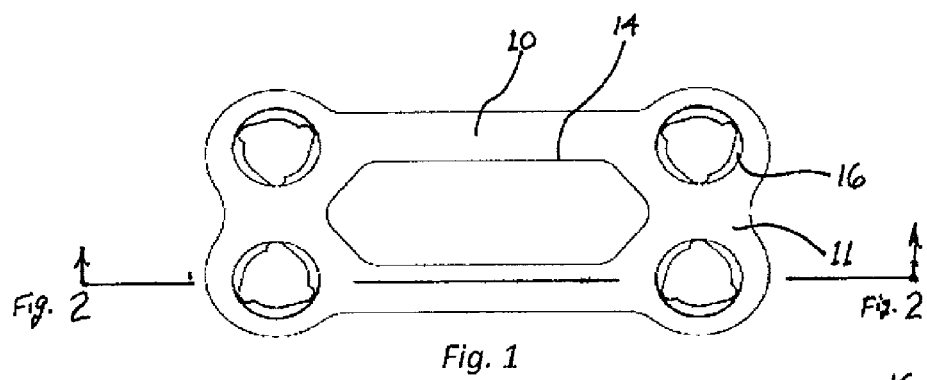
FIG. 1 is a top view of a cervical fixation plate according to one embodiment.
Figure 2:
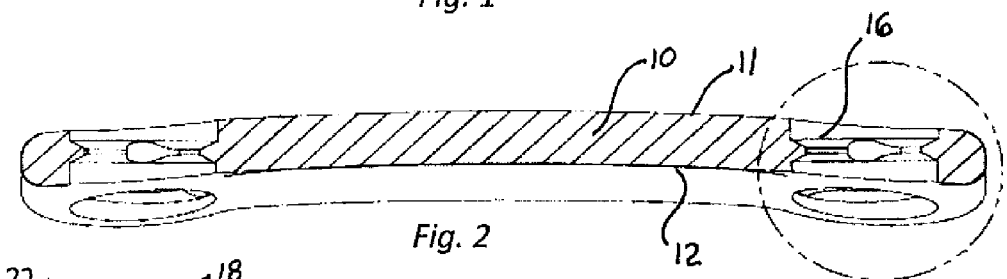
FIG. 2 is a side cross-sectional view of the plate shown in FIG. 1, taken along line 2-2 as viewed in the direction of the arrows.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring to FIGS. 1-7, a cervical fixation plate 10 is depicted that includes a central cut-out 14 and four bone screw bores 16 defined at the corners of the generally rectangular plate. The lower surface 12 of the plate is configured or contoured for minimal prominence when the plate is mounted to adjacent cervical vertebrae. Similarly, the upper surface 11 is fashioned to maintain a smooth profile to avoid irritation to the soft tissue surrounding the implanted plate. The length and curvature of the plate may be configured in a known manner for implantation at a particular cervical level. Similarly, the location of the bone screw bores 16 may be in accordance with known standards, with a primary object being to locate the bone screws for solid engagement in the cervical vertebral body. In one embodiment, the longitudinal axes of the screw bores are parallel to each other, rather than expressly to the top or bottom surfaces 11, 12 of the plate. Thus, in one specific embodiment, the top surface 11 is gently curved, while the axes of the screw bores 16 are offset by about five degrees relative to a normal axis to the top surface. This angular offset may be inboard relative to the normal axis.

Figure 8:
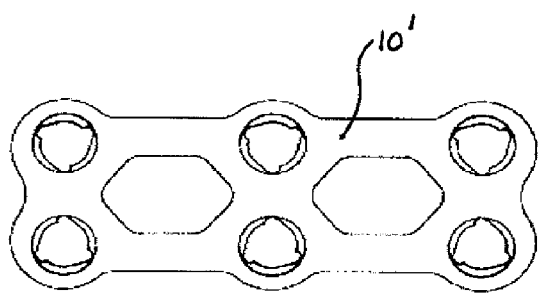
FIG. 8 is a top view of an alternative plate incorporating the present invention.
Figure 9:
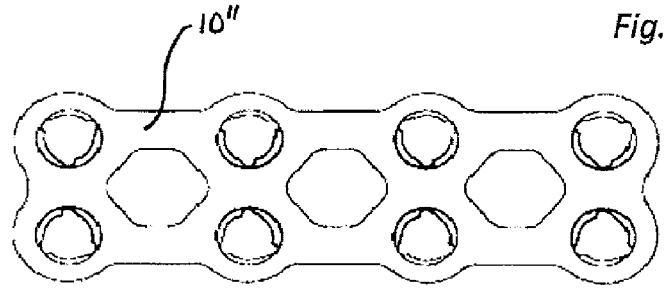
FIG. 9 is a top view of another alternative plate incorporating the present invention.

The fixation plates 10' and 10" shown in FIGS. 8-9 further illustrate the configurations of fixation plates for instrumenting various vertebral levels, particularly in the cervical spine. The plate 10 includes two sets of bone screw bores for engaging two vertebral bodies, while the plate 10' includes three screw bore pairs for engaging a corresponding number of vertebrae. Likewise, the four sets of screw bores in the plate 10" permits fixation to four vertebral bodies.

Turning to FIGS. 3-6, details of the plate 10 are shown, and more particularly details of the screw bores 16. In accordance with one feature of the invention, the screw bores are configured to be self-locking at a range of angles, perpendicular and non-perpendicular, to the bottom surface 12 of the plate. The screw bores include an inner surface adapted to receive a bone screw therethrough, in which the inner surface includes an upper portion 18 extending from the top plate surface 11 and a lower portion 20 extending upward from the bottom plate surface 12. The two portions are separated by a rib element 22 projecting from the inner surface having an upper surface 23 angled upward toward the upper portion 18 and a lower surface 24 angled downward toward the lower portion 20. The two surfaces 23, 24 converge to an inner edge 25 that has a thickness t. In the preferred embodiment, this thickness t is non-zero, yet small enough to fit within the thread pitch of a bone screw (such as screw 40 in FIG. 10) engaged therein, as explained in more detail herein. In a specific embodiment, the upper and lower surfaces 23, 24 subtend an angle of 60 degrees to correspond to the pitch of the bone screw thread.

In the illustrated embodiments, the upper and lower portions 18, 20 are depicted as having the same depth. In these embodiments, the rib element 22 is thus oriented at mid-thickness of the plate. In alternative embodiments, the rib element 22 may be offset toward one or the other of the top and bottom surfaces 11 and 12 of the plate 10. In addition, the upper and lower portions are shown as cylindrical, although other configurations are contemplated, such as conical or spherical.

Figure 3:
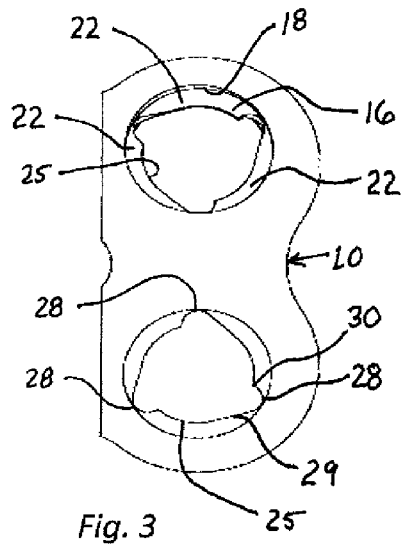
FIG. 3 is a top view of an end portion of the plate shown in FIG. 1.
Figure 4:
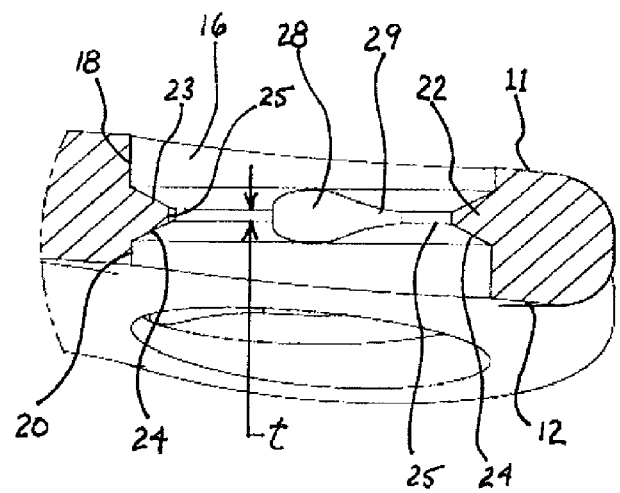
FIG. 4 is an enlarged cross-sectional view of the plate shown in FIG. 2.
Figure 5:
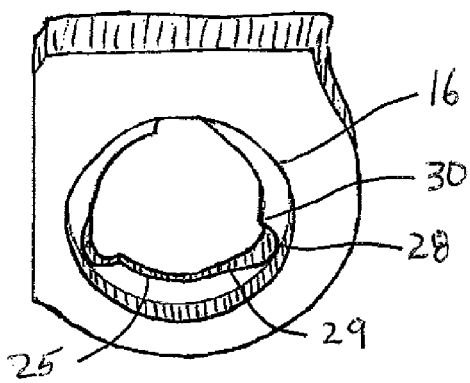
FIG. 5 is an enlarged top perspective view of a screw bore of the plate shown in FIG. 1.
Figure 6:
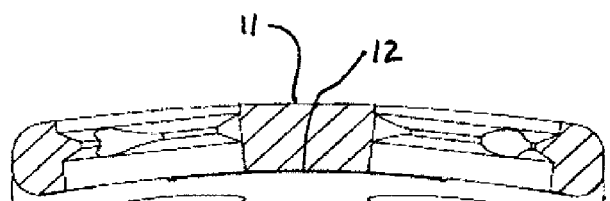
FIG. 6 is an end perspective partial cut-away view of the plate shown in FIG. 1.
Figure 7:
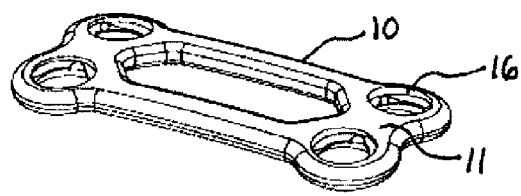
FIG. 7 is a perspective view of the plate shown in FIG. 1.

In one feature of the invention, the rib element 22 includes a number of scallops 28, as best seen in FIGS. 3 and 5. The scallops 28 are generally defined by circular cuts through the rib element 22 with the axis of the scallops running generally parallel to the axis of the corresponding screw bore 16. The scallops 28 include a linear scallop run-out 29 that merges to the inner edge 25 of the rib element. With the scallop runout, the radius of the inner edge 25 thus becomes non-uniform around the circumference of the rib element. Thus, the inner edge 25 follows a constant radius from a scallop corner 30 at each scallop for about one-third of the circumferential distance between successive scallops, for a screw bore having three such scallops. The scallop run-out extends generally tangentially from the scallop diameter and merges tangentially with the inner edge of the rib, as best seen in FIG. 3. The scallop run-out 29 is oriented in the direction of tightening a threaded fastener, which in the embodiment illustrated in FIG. 3 is in the clockwise direction. In other words, the point at which the scallop run-out merges with the inner edge 25 of the rib element 22 is offset clockwise from the origin of the run-out at the scallop 28.

By way of example, in one specific embodiment, the upper and lower portions 18, 20 of the screw bores 16 have a diameter of 5.40 mm. The scallops 28 are defined at a radius of 0.60 mm, with the center axis being aligned with the inner diameter of the inner edge 25, which in the specific embodiment is 4.20 mm. In this embodiment, three scallops are provided that are circumferentially offset by 120 degrees. Thus, each scallop run-out 29 extends tangentially from the scallop diameter and continues clockwise about two-thirds of the circumferential offset between successive scallops, or about 80 degrees from the originating scallop.

In the illustrated embodiments, each screw bore 16 includes three scallops 28 uniformly spaced around the circumference of the bore. It can be appreciated that other numbers of scallops may be provided in each screw bore, with different numbers of scallops in each bore of a given plate. As explained herein, the scallops permit different angular orientations of a bone screw relative to the plate, with the number of orientations being a function of the number of scallops.

Figure 10:
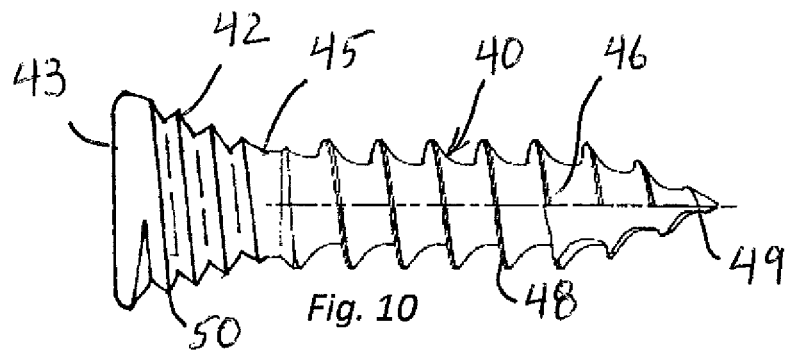
FIG. 10 is a side perspective view of a bone screw according to a further embodiment disclosed herein.
Figure 11:
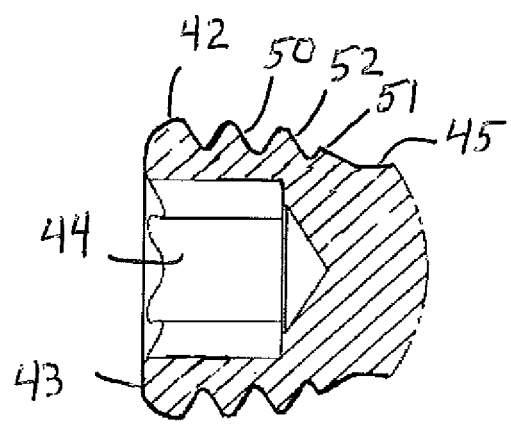
FIG. 11 is an enlarged view of a portion of the head of the bone screw shown in FIG. 10.

Turning to FIGS. 10-11, details can be discerned of one embodiment of a bone screw adapted to engage the screw bores 16 of the cervical plate 10. The bone screw 40 includes a head 42 which may including a drive recess 44 configured to accept a standard driving tool, such as a hex or TORX® driver. The shank 46 of the screw includes bone-engaging threads 48, and may incorporate a self-tapping tip 49. The bone engaging threads may have a variety of configurations.

The length of the shank 46, as measured from below the head 42, is adapted to the particular bone in which the screw is to be engaged. Thus, in one specific embodiment, a cervical screw can be provided in lengths of 12.0 or 14.0 mm, with the head having a length of 3.5 mm. The length of the shank 46 is thus 8.5 or 10.5 mm. Thus, the bone engaging threads 48 will engage the vertebral body to a minimum depth corresponding to length of the shank. Depending upon the depth of engagement of the head 42 of the bone screw 40 within the cervical plate 10, the shank may be embedded deeper into the bone, but no greater than the total length of the screw less the thickness of the plate.

The head 42 of the screw 40 incorporates a feature adapted to engage the rib element 22 of the bone plate 10. In particular, the head 42 incorporates a gradually decreasing diameter from the upper surface 43 to the intermediate portion 45 between the head and the shank 46. The diameter at the upper surface 43 is less than the diameter of the upper portion 18 of the screw bores 16 but greater than the inner diameter of the inner edge 25 of the circumferential rib element 22. The diameter of the head 42, or more specifically the root diameter of the locking threads 50 described below, decreases to a diameter that is slightly less than the inner diameter of the inner edge 25. (Of course, the outer diameter of the bone engaging threads 48 is less than the inner diameter of the rib element to permit introduction of the shank 46 through the screw bore 16.)

The head 42 includes locking threads 50 that are adapted to engage the rib element 22 of the screw bore. In one embodiment, the root diameter of the threads is tapered inward from the upper surface 43 of the head to the intermediate portion 45. The outer diameter of the threads is parallel to the root diameter, with the exception of the lead thread 51. The lead thread 51 has a thread height that is about half the thread height of the remainder of the locking threads 50 to facilitate introduction of the locking threads into the screw bore 16. In one embodiment, the thread faces 52 subtend an angle different from the subtended angle of the upper and lower surfaces 23, 24 of the rib element 22. Thus in one specific embodiment, the thread faces 52 are at an angle of 50 degrees relative to the longitudinal axis of the screw to subtend an 80 degree angle.

Figure 12:
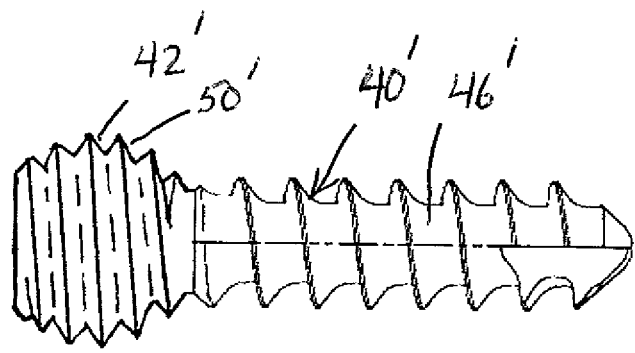
FIG. 12 is a side view of an alternative bone screw.

In an alternative embodiment shown in FIG. 12, the head 42' of the bone screw 40' may be spherical. The shank 46' may be configured like the shank 46 just described for engagement with the cervical bone. The locking threads 50' thus follow the spherical contours of the head 42'. The thread faces in this embodiment may subtend an angle that is the same as the subtended angle of the rib element 22 surfaces. The locking threads may also be double threads starting 180 degrees apart.

Figure 13A:
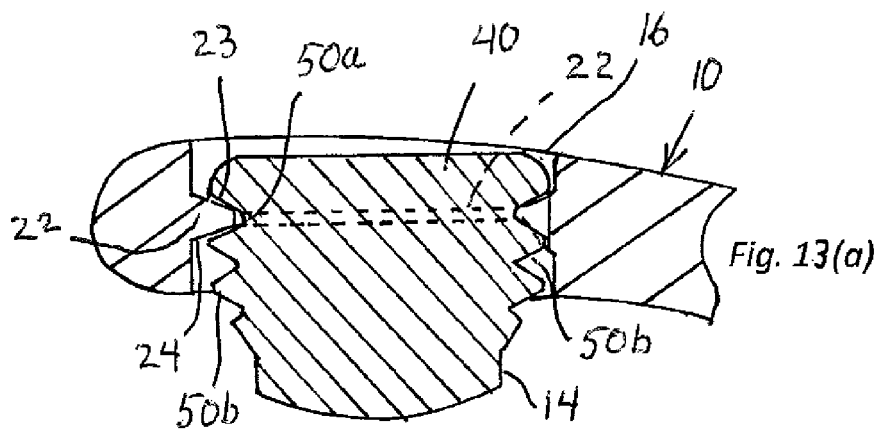
FIGS. 13(a)-(c) are partial cross-sectional views of a screw bore of the cervical plates disclosed herein with a bone screw engaged at different angles relative to the plate.
Figure 13B:
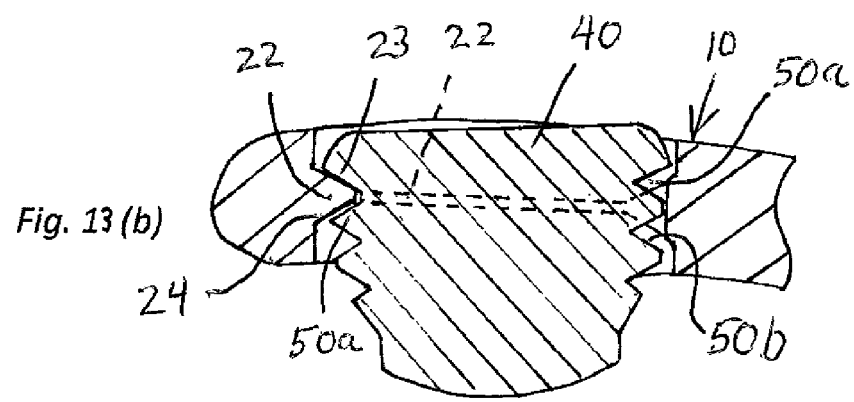
Figure 13C:
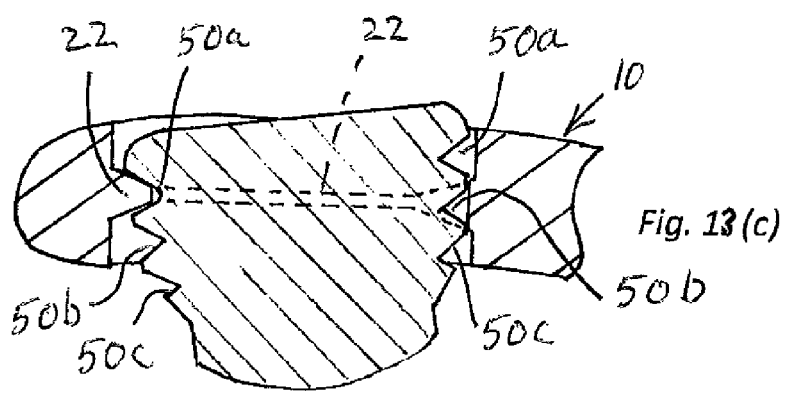

As depicted in FIGS. 13(*a*)-(*c*), the locking threads can engage the rib element 22 in different ways to achieve different angular orientations relative to the plate 10. As shown in FIG. 13(*a*), the screw 40 can be positioned substantially perpendicular to the plate by threading the screw directly into the opening 16 and through the inner diameter defined by the inner edge 25 of the rib element 22. In this instance, the root of the uppermost thread 50*a* spans the upper and lower surfaces 23, 24 of the rib element 22. T In FIG. 13(*b*), the screw 40 is oriented at an angle relative to the plate, which in the illustrated embodiment is about eight degrees. In this orientation, the uppermost thread 50*a* contacts the upper surface 23 of the rib element 22 while the next thread 50*b* contacts the lower surface 24 of the rib element at a circumferentially offset location. In other words, while the thread 50*a* contacts the upper surface of the rib adjacent one scallop, the thread 50*b* will contact the lower surface of the rib adjacent another scallop.

In order to achieve a larger angular orientation, the first thread 50*a* contacts the upper surface 23 of the rib element 22 at a sharper angle, and even dig into the rib element. The second thread 50*b* also engages the upper surface 22 at a sharper angle so that the next thread 50*c* may dig into the lower surface 24 of the rib element. In a specific embodiment, the screw 40 can thus achieve an angle of fifteen degrees relative to the plate.

In one aspect of the illustrated embodiments, one side of the locking threads 50 provides a typical peak-to-valley mating, as exemplified by the engagement of the uppermost thread 50*a* with the lower surface 24 of the rib element 22. It can be appreciated that this same peak-to-valley engagement occurs even if the screw 40 is not fully threaded into the screw bore as depicted in the figures. For example, if the screw is backed out one turn, the second thread 50*b* will engage the lower surface with the uppermost thread 50*a* contacting the upper surface of the rib element. In this configuration, the rib element—the peak—will fit within the thread pitch—the valley.

However, the thread engagement 180 degrees offset from the peak-to-valley engagement is an interference fit with the rib element 22. For instance, in the arrangement shown in FIG. 13(*a*), the second thread 50*b* will dig into the rib element 22 as the screw 40 is driven into the screw bore. The presence of the scallops 28 and scallop run-outs 29 allow the locking threads to be initially threaded into the bore as the lowermost thread passes through one of the scallops. Moreover, the scallops allow the screw 40 to be driven into the screw bore in any of the orientations shown in FIGS. 13(*a*)-(*c*). In general terms, the screw 40 will adopt the angle that the lowermost thread of the locking threads enters the first scallop.

This feature of the present invention allows the surgeon to drive the bone screw at the optimum angle for maximum engagement and fixation within the vertebral bone. During implantation, the screw bore 16 of the cervical plate 10 initially acts as a guide for placing the bone screw. The bone engaging threads 48 are driven into the vertebral bone at any desired angle. As the bone engaging threads are driven to their fullest extent into the bone, the locking threads contact the bone plate, and particularly the rib element. For a three scallop configuration, the screw 40 need only be rotated a maximum of 80 degrees before the lowermost thread will reach a scallop 28. The scallop and the scallop runout 29 allow the lowermost thread to fully engage the rib element 22 so that continued rotation of the screw will draw the successive threads into engagement without risk of being dislodged at a downstream scallop.

Once the locking threads have been threaded to their fullest extent into the screw bore, the interface becomes self-locking In particular, the scallop corner 30 (see FIG. 5) formed at the interface between each scallop and the full diameter portion of the rib element prevents the screw from backing out or counter-rotating. In particular, any counter-rotation will cause the scallop corner 30 to dig into the locking threads 50 of the screw 40. It can be appreciated that the rib element 22 is not configured as a screw thread, but instead as a ring embedded within the screw bore. Consequently, when the threads of the screw are counter-rotated, they are not following a normal thread contour, but must instead immediately contact the scallop corner 30 at each scallop 28.

It can thus be appreciated that the scallops 28 provided in the screw bore 16 provide multiple benefits. One significant benefit is that the scallops allow the bone screw to adopt a range of non-perpendicular angular orientations without the need for additional hardware found in prior screw-plate designs. Another benefit is that there is no need for forming female threads within the plate, which typically requires a thicker plate. Thus, with the single rib configuration of the present invention, the cervical plate 10 may be thinner than prior plate designs. A thinner plate means a lower profile and lower prominence, which in turn avoids soft tissue irritation that can often accompany fixation plates. A further benefit is that the same structure that facilitates driving the bone screw in at multiple angles also provides a self-locking or anti-backout features, again without the need for additional hardware founding prior screw-plate designs.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The bone plate and screw embodiments described herein have been for use in fixation of the cervical spine. It is understood that the same principles may be employed at other locations in the spine, such as in the lumbar spine, and for other types of fixation. For instance, the embodiments described herein may be modified for use in compression of bone fractures or immobilization of joints, such as the bones and joints of the hands and feet. The variable angular orientations and the self-locking features of the described embodiments may be implemented in a variety of environments for fixation of a plate to a bone. It is further contemplated that these features may be implemented in the fixation of plate segments that may be used to fasten an elongated rod, for instance, to a bone.

What is claimed is:

1. A bone fixation assembly comprising:
   a plate having a top surface and a bottom surface and defining at least one bore between said surfaces, said bore including an inner surface and only one circumferential rib projecting outwardly from said inner surface toward the interior of said bore substantially continuously around said inner surface and situated between said top and bottom surfaces of said plate such that the circumferential rib is spaced apart from the top surface and the bottom surface, said bore further defining at least one scallop interrupting said circumferential rib only once; and
   a bone engaging fastener corresponding to each of said at least one bore, said fastener having a shank defining bone engaging threads and a head, said head defining helical locking threads for threaded engagement with said circumferential rib, said helical locking threads including a lead thread configured to pass through said scallop to allow said helical locking threads to engage said circumferential rib.

2. The bone fixation assembly according to claim 1, wherein said bore defines three scallops substantially evenly distributed around the circumference of said circumferential rib.

3. The bone fixation assembly according to claim 1, wherein said at least one bore includes four substantially identically configured bores.

4. The bone fixation assembly according to claim 1, wherein:
   said plate is a substantially rectangular plate sized and shaped for fixation between at least two adjacent cervical vertebrae;
   said at least one bore includes four bores, one each situated at each corner of said substantially rectangular plate; and four bone engaging fasteners are provided for engagement within a corresponding one of said four bores.

5. The bone fixation assembly according to claim 4, wherein each of said four bores is substantially identically configured and each of said four bone engaging fasteners is substantially identically configured.

6. The bone fixation assembly according to claim 1, wherein:
said circumferential rib defines an inner edge; and
said bore further defines a scallop run-out extending tangentially from a scallop to said inner edge.

7. The bone fixation assembly according to claim 6, wherein said scallop run-out merges substantially tangentially with said inner edge.

8. The bone fixation assembly according to claim 6, wherein said bore defines three scallops substantially evenly spaced apart 120 degrees around the circumference of said circumferential rib, each scallop including a corresponding scallop run-out extending from said scallop and merging with said inner edge substantially 80 degrees from the tangential intersection of said run-out with said scallop.

9. The bone fixation assembly of claim 1, wherein said shank of said bone engaging fastener is sized to pass freely through said circumferential rib.

10. The bone fixation assembly of claim 1, wherein said bore defines a sharp corner between said at least one scallop and said circumferential rib.

11. The bone fixation assembly according to claim 1, wherein said circumferential rib is at a non-perpendicular angle relative to a longitudinal axis of said bore extending between said top and bottom surfaces.

12. The bone fixation assembly according to claim 1, wherein said at least one scallop is defined by circular cuts through said rib with an axis of the scallop extending between said top and bottom surfaces and running generally parallel to a longitudinal axis of said bore extending between said top and bottom surfaces.

13. The bone fixation assembly according to claim 6, wherein:
said inner edge defines an inner diameter; and
said one scallop run-out merges tangentially with said inner diameter.

14. The bone fixation assembly according to claim 6, wherein said one scallop run-out extends tangentially from the associated scallop in a clockwise direction.

15. The bone fixation assembly according to claim 14, wherein said bore defines a sharp corner between said at least one scallop and said circumferential rib counterclockwise from said scallop run-out.

16. A bone fixation plate comprising:
a top surface and an opposite bottom surface; and
at least one bore defined between said surfaces, said bore including an inner surface and only one circumferential rib projecting outwardly from said inner surface toward the interior of said bore substantially continuously around said inner surface and situated between said top and bottom surfaces of said plate such that the circumferential rib is spaced apart from the to surface and the bottom surface, said circumferential rib defining an inner edge radially offset from said inner surface toward the interior of said bore, said bore further defining at least one scallop interrupting said circumferential rib and one scallop run-out associated with each scallop extending tangentially from the associated scallop to said inner edge.

17. The bone fixation plate according to claim 16, wherein said bore defines three scallops substantially evenly spaced apart 120 degrees around the circumference of said circumferential rib, each scallop including a corresponding scallop run-out extending from said scallop and merging with said inner edge substantially 80 degrees from the tangential intersection of said run-out with said scallop.

18. The bone fixation plate of claim 16, wherein said bore defines a sharp corner between said at least one scallop and said circumferential rib.

19. The bone fixation plate according to claim 16, wherein said at least one scallop is defined by circular cuts through said rib with an axis of the scallop extending between said top and bottom surfaces and running generally parallel to a longitudinal axis of said bore extending between said top and bottom surfaces.

20. The bone fixation assembly according to claim 16, wherein:
said inner edge defines an inner diameter; and
said one scallop run-out merges tangentially with said inner diameter.

* * * * *